(12) United States Patent
Musa et al.

(10) Patent No.: US 7,928,245 B2
(45) Date of Patent: Apr. 19, 2011

(54) ALCOHOLS CONTAINING IMIDE MOIETIES AND REACTIVE OLIGOMERS PREPARED THEREFROM

(75) Inventors: Osama M. Musa, Hillsborough, NJ (US); Brian Marr, Hampton, NJ (US)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 12/693,781

(22) Filed: Jan. 26, 2010

(65) Prior Publication Data

US 2010/0190998 A1 Jul. 29, 2010

Related U.S. Application Data

(63) Continuation of application No. PCT/US2007/074463, filed on Jul. 26, 2007.

(51) Int. Cl.
*C07D 403/14* (2006.01)
(52) U.S. Cl. ........................................................ 548/455
(58) Field of Classification Search .................... None
See application file for complete search history.

(56) References Cited

U.S. PATENT DOCUMENTS

| 5,084,345 | A | * | 1/1992 | Manos | 428/335 |
| 2005/0222427 | A1 | | 10/2005 | Sharpless et al. | |
| 2007/0167544 | A1 | * | 7/2007 | Pal et al. | 524/115 |

FOREIGN PATENT DOCUMENTS

EP 1507769 A1 2/2005

OTHER PUBLICATIONS

Zentz, et al., Il Farmaco, 57:421 (2002).*

Kolb, H.C. et al. Click Chemistry: Diverse Chemical Function from a Few Good Reactions. Angew. Chem. Int. Ed. 2001, 40, 2004-2021.

* cited by examiner

*Primary Examiner* — Yong Chu
*Assistant Examiner* — Michael Barker
(74) *Attorney, Agent, or Firm* — Jane E. Gennaro

(57) ABSTRACT

This invention relates to oligomeric compounds that are prepared by the reaction of a dianhydride with an amino-alcohol to yield an imide-diol intermediate, which is then esterified with a carboxylic acid to form a reactive oligomer. An exemplary reaction scheme is the following:

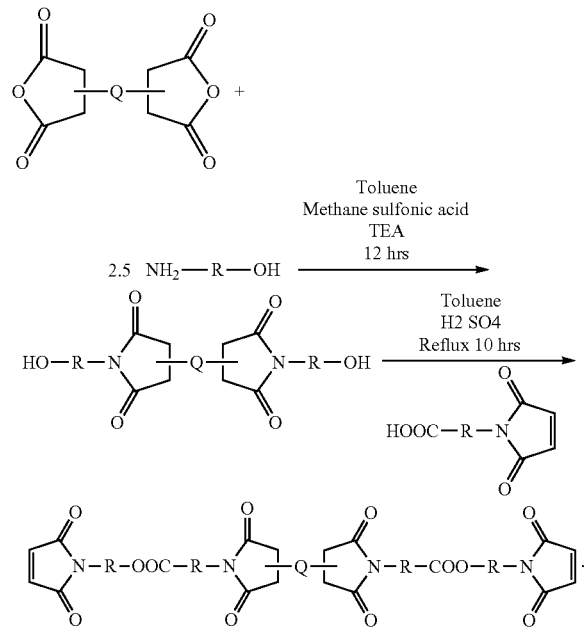

9 Claims, No Drawings

ALCOHOLS CONTAINING IMIDE MOIETIES AND REACTIVE OLIGOMERS PREPARED THEREFROM

CROSS-REFERENCE TO RELATED APPLICATION

This application is a continuation of International Application No. PCT/US2007/074463 filed Jul. 26, 2007, the contents of which are incorporated herein by reference.

BACKGROUND OF THE INVENTION

This invention relates to alcohols containing imide moieties and to reactive oligomeric compounds prepared from those alcohols. The reactive oligomeric compounds are useful as adhesives, coatings, and encapsulants, and are particularly useful for various fabrication steps in semiconductor packaging.

Adhesives, coatings, and encapsulants for use on metal, glass, and plastic surfaces have many applications within various industries. Adhesion to these surfaces in general is difficult and new compounds or formulations are sought for both quick and strong adherence. Such materials would be particularly useful within the semiconductor packaging industry. Common steps in the fabrication of semiconductor packages involve affixing semiconductor devices onto substrates or encapsulating or coating parts or all of the device. The more prominent steps that use adhesives, coatings or encapsulants are the bonding of integrated circuit chips to lead frames or other substrates, the bonding of circuit packages or assemblies to printed wire boards, the encapsulation of solder balls used as electrical connections, coating the active or inactive face of silicon wafers, and the coating of via holes. In these applications, the components of the assembly are prepared from different materials, such as metal, glass, silicon, and plastic, and the adhesive, coating, or encapsulant must bond to the surface of each. Moreover, the adhesive, coating, or encapsulant must maintain its bond to both materials through temperature and humidity cycles. Thus, there is always a need for new compounds and formulations within the semiconductor packaging industry and within other industries using components that must adhere to more than one type of surface.

SUMMARY OF THE INVENTION

This invention relates to alcohols having at least one imide moiety, and to the reaction products of the hydroxyl group of those alcohols with complementary reactive functionality, such as, a halide, an acid, an amine, or an isocyanate. The alcohols are formed by the reaction of an anhydride with an amino-alcohol to yield an imide-linked alcohol. This alcohol can be further reacted with a compound having (1) a functionality to react with the hydroxyl group of the alcohol, such as an organic halide, acid, amine, or isocyanate, and (2) a second functionality that is capable of homo-polymerization, or polymerization with another functionality, not reactive with the hydroxyl functionality. This second functionality can be used for later cure, and can be, for example, a maleimide; an acrylate or methacrylate; a styrene or a cinnamyl; a maleate or a fumarate; an alkyne, such as a propargyl ether or a propargyl amine; a vinyl ether, an epoxy, an oxetane, or an episulfide; a benzoxazine or oxazoline; cyanate ester; an azide; or a silane. The reaction of the alcohol produces an oligomeric compound, which in another embodiment of this invention can be used in adhesive, coating, and encapsulant compositions, curing with the homo-polymerization or the hetero-polymerization of the second reactive functionality.

An exemplary reaction scheme for forming the alcohol and an oligomer from that alcohol, in which the second functionality on the alcohol is a maleimide, is as follows:

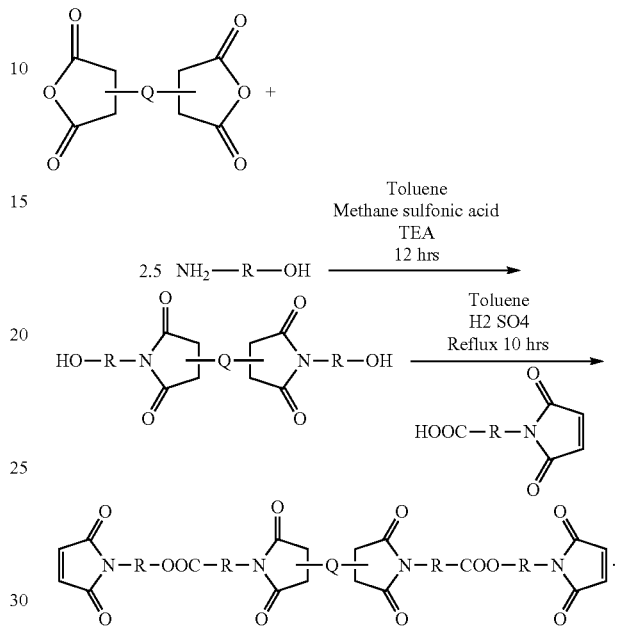

in which R, R', and Q independently can be an aliphatic or aromatic moiety, which may contain one or more heteroatoms. In this case and using this process, there is only one ring closure from amic acid and the resulting end product is a di-functional (reactive) oligomer that has imide and ester linkages.

DETAILED DESCRIPTION OF THE INVENTION

The formation of the imide containing alcohol occurs with the reaction of an anhydride with an amino alcohol. The anhydride can be mono- or multi-functional, and can be aliphatic or aromatic. There is no limit to the number of anhydride functionalities that can be present; in various embodiments, the anhydride will have one to four anhydride functionalities in one molecule.

Exemplary anhydrides include 1,2,4-benzenetricarboxylic anhydride, cis-5-norbornene-endo-2,3-dicarboxylic anhydride, 1,2-cyclohexanedicarboxylic anhydride, cis-1,2,3,6-tetrahyydrophthalic anhydride, 3,4-pyridinedicarboxylic anhydride, homophthalic anhydride, 2-methylenesuccinic anhydride, methyl-5-norbornene-2,3-dicarboxylic anhydride, and 3,1-benzoxazine-2,4(1H)-dione.

Exemplary dianhydrides include 4,4'-(hexafluoro-isopropylidine)bisphthalic anhydride (6FDA), 4,4'-bisphenol A dianhydride, benzene-1,2,4,5-tetracarboxylic dianhydride, 1,4,5,8-naphthalenetetracarboxylic diandydride, diethylenetriamine-pentaacetic acid dianhydride, bicyclo[2.2.2]oct-7-ene-2,3,5,6-tetracarboxylic dianhydride, perylene-3,4,9,10-tetracarboxylic dianhydride, 3,3'4,4'-biphenyltetracarboxylic dianhydride, benzophenone-3,3'4,4'-tetracarboxylic diahydride.

Exemplary multi-functional anhydrides include maleic anhydride functionalized polybutadiene resins available from Sartomer under the tradename RICON, such as, RICON 10MA, RICON 13MA, and RICON 17MA.

Suitable multifunctional anhydrides may also be synthesized according to the following reaction scheme:

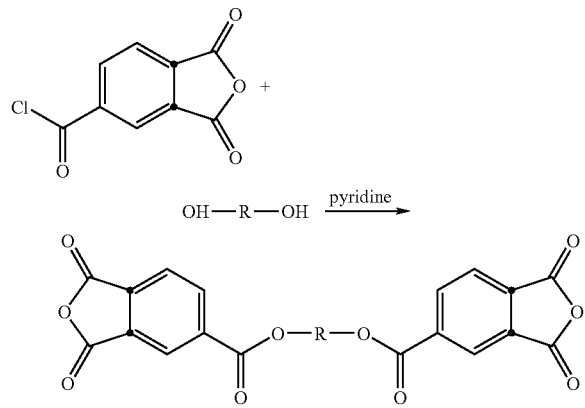

in which R can be any aromatic or aliphatic entity. Exemplary R moieties include

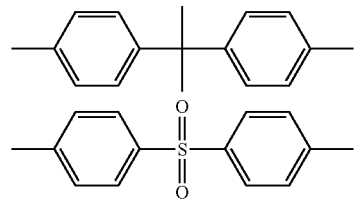

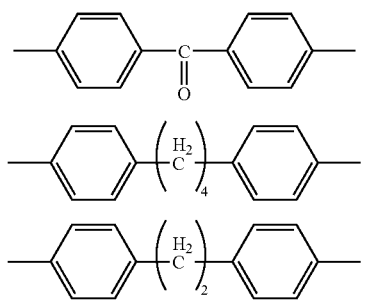

-continued

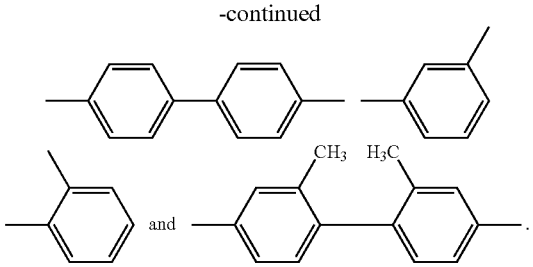

It is possible to start with a tri- or tetra-alcohol, or any multifunctional alcohol, and perform the same synthesis to obtain multi-functional anhydrides.

The amino alcohol used to react with the anhydride can be aliphatic or aromatic. Exemplary amino-alcohols include 4-aminophenylethanol, 3-amino-1-propanol, 2-amino-1-phenylethanol, (R)-2-amino-2-phenylethanol, 1-(3-aminophenyl)ethanol, and 2-amino-3-methylbenzyl alcohol.

Exemplary alcohols having imide linkages are prepared by reacting the anhydride with the amino alcohol in the presence of triethylamine in toluene using methanesulfonic acid as the catalyst. The reaction is stirred for one hour at room temperature and then heated to reflux for 10 to 15 hours, or until nearly all theoretical water generated by the reaction is collected. The reaction is then cooled to room temperature and allowed to phase-out. The top colorless phase is discarded and the bottom phase dissolved in dichloromethane and washed twice with 5% hydrogen chloride solution. These washes serve to protonate and remove residual/excess 4-aminophenethyl alcohol. The efficiency of these washes can be monitored by TLC eluting in a 5/1 (volume) acetone/methanol solvent system. The acid washes are followed by distilled water washes, after which the organic phase is collected and dried over magnesium sulfate. Solvent is stripped from the solution to yield the alcohol.

Exemplary alcohols having imide linkages are

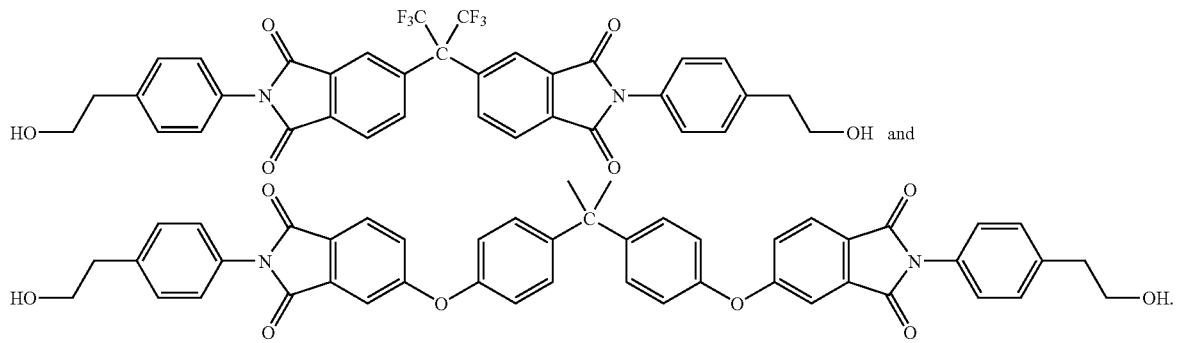

The resulting imide linked alcohols can be reacted with a multi-functional organic compound having (1) at least one functionality reactive with the hydroxyl functionality of the alcohol, and (2) at least one functionality that can homo-polymerize or hetero-polymerize to cure. In general, the functionality that can polymerize should not be reactive with hydroxyl functionality.

The functionalities reactive with hydroxyl are selected from the group consisting of halide, acid, amine, epoxy, and isocyanate; the functionalities for polymerization, not reactive with hydroxyl, are selected from the group consisting of maleimide, acrylate, methacrylate, styrene, cinnamyl, maleate, fumarate, propargyl ether, propargyl amine, vinyl ether, epoxy, oxetane, benzoxazine, oxazoline, cyanate ester, azide and silane.

Examples of multi-functional compounds suitable for reaction with the imide linked alcohols include, but are not limited to,

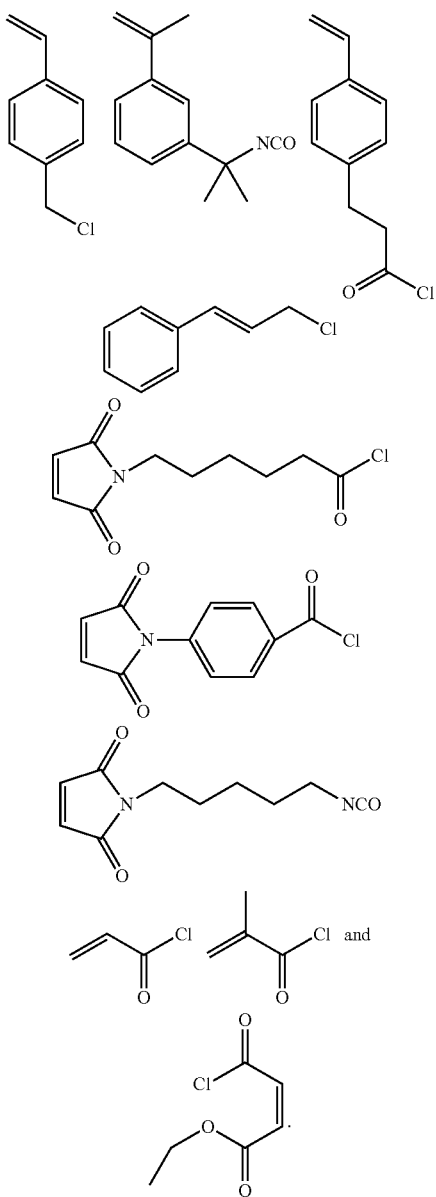

Other suitable compounds for reacting with the imide containing alcohols are maleimide acids, which are compounds containing both maleimide and acid functionality. A maleimide acid is prepared by reacting a molar equivalent of maleic anhydride with a molar equivalent of an amino acid to form an amic acid and dehydrating the amic acid to form a maleimide acid.

Suitable amino acids for forming the maleimide acids can be aliphatic or aromatic, and include, but are not limited to, glycine, alanine, 2-aminoisobutyric acid, valine, tert-leucine, norvaline, 2-amino-4-pentenoic acid, isoleucine, leucine, norleucine, beta-alanine, 5-aminovaleric acid, 6-aminocaproic acid, 7-aminoheptanoic acid, 8-aminocaprylic acid, 11-amino-undecanoic acid, 12-aminododecanoic acid, 2-phenylglycine, 2,2'-diphenylglycine, phenylalanine, alpha-methyl-DL-phenylalanine, and homophenylalanine.

Other suitable compounds for reacting with the imide alcohols are the metal salts of a maleimide. The metal salt of a maleimide is prepared by reacting maleic anhydride with an amino acid. The maleic anhydride is dissolved in an organic solvent, such as acetonitrile, and this solution added to a one mole equivalent of the desired amino acid. The mixture is allowed to react, typically for about three hours, at room temperature, until white crystals are formed. The white crystals are filtered off, washed with cold organic solvent (acetonitrile) and dried to produce the amic acid adduct. The amic acid adduct is mixed with base, typically triethylamine, in a solvent, such as toluene. The mixture is heated to 130° C. for two hours to dehydrate the runic acid and form the maleimide ring. The organic solvent is evaporated and sufficient 2M HCL added to reach pH 2. The product is then extracted with ethyl acetate and dried, for example, over $MgSO_4$, followed by evaporation of the solvent.

The products from the above reaction are compounds containing both maleimide and carboxylic acid functionalities. It will be understood by those skilled in the art that the hydrocarbon (aliphatic or aromatic) moiety separating the maleimide and acid functionalities is the derivative of the starting amino acid used to make the compound.

Compounds containing a functionality reactive with hydroxyl functionality, and either an alkyne or an azide functionality are also suitable reactants. If an compound containing alkyne is used to react with the alcohol, then it is possible to react the alkyne functionality in the resultant compound in a later polymerization with a compound containing an azide functionality; likewise, if an azide compound is used, it will be possible to react the azide functionality in the resultant compound in a later polymerization with a compound containing an alkyne functionality. These azide/alkyne reactions are well known from Sharpless and co-workers of Scripps Research Institute, in US patent application 2005/0222427 and in EP patent 1507769, which described a copper (I)-catalyzed ligation process of azides and alkynes in solution phase using Cu(II) salts in the presence of a reducing agent, such as sodium ascorbate. These reactions furnished triazole polymers under ambient conditions. See also, H. C. Kolb, M. G. Finn and K. B. Sharpless, *Angew. Chem. Int. Ed.* 2001, 40, 2004-2021.

In the reactions with the alcohols, more than one di- or multi-functional compound can be used in the reaction mix, so that it is possible to obtain oligomers that contain two different terminal reactive functionalities, for example, but not by way of limitation, maleimide and acrylate functionality, styrene and acrylate functionality, cyanate ester and silane functionality, epoxy and acrylate functionality, vinyl ether and maleimide functionality.

The synthetic processes for making the inventive oligomers from the imide linked alcohols are illustrated in the examples in this specification. In essence, the alcohol is reacted with an excess of the di- or multi-functional organic compound, for example a carboxylic acid having vinyl functionality in a Fischer esterification.

In another embodiment, this invention is a curable composition comprising the inventive oligomers. The inventive oligomers may be present either as the major or as a minor curable component in the composition. The composition may also comprise other resins or polymers, curing agents, adhesion promoters, fillers, wetting agents, fluxing agents, and other such components commonly used in curable compositions. Curable compositions are used, for example, as adhesive, coating, and encapsulation formulations and end uses.

Any resins and polymers used in the formulation, in addition to the inventive oligomers, may be solid, liquid, or a combination of the two. Suitable additional resins and polymers include epoxies, acrylates and methacrylates, maleimides, bismaleimides, vinyl ethers, polyesters, poly(butadienes), siliconized olefins, silicone resins, siloxanes, styrene resins and cyanate ester resins.

Exemplary solid aromatic bismaleimide (BMI) resin powders for use in formulations with the inventive oligomers, are those having the structure

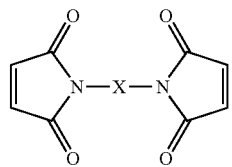

in which X is an aromatic group. Exemplary aromatic groups include:

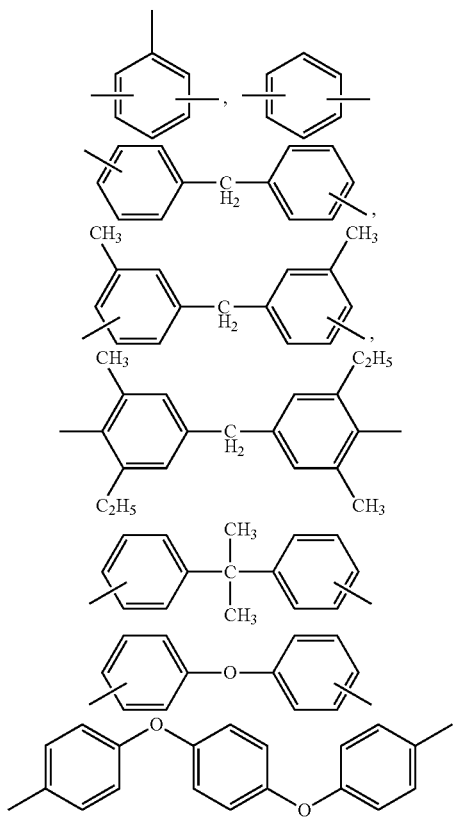

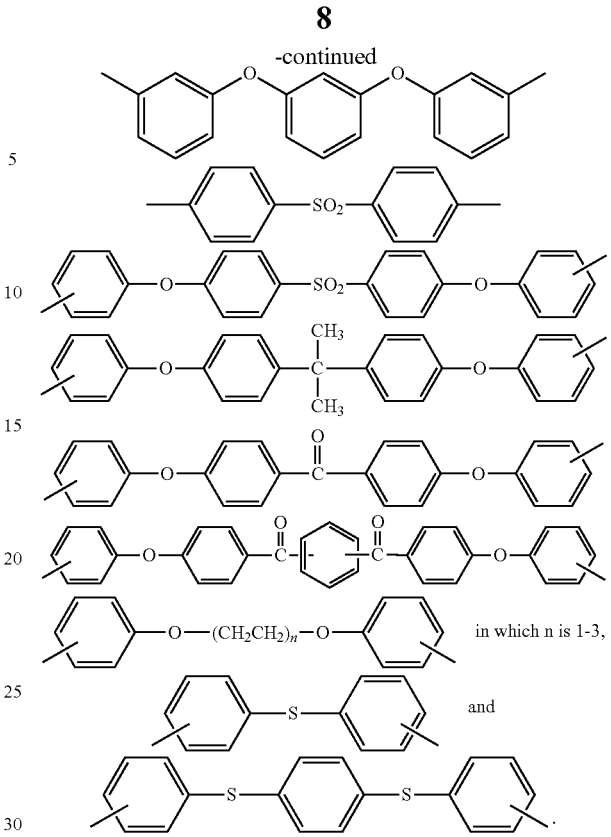

in which n is 1-3, and

Bismaleimide resins having these X bridging groups are commercially available, and can be obtained, for example, from Sartomer (USA) or HOS-Technic GmbH (Austria).

Additional exemplary maleimide resins for use in formulations with the inventive oligomers include those having the generic structure

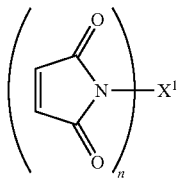

in which n is 1 to 3 and $X^1$ is an aliphatic or aromatic group. Exemplary $X^1$ entities include, poly(butadienes), poly(carbonates), poly(urethanes), poly(ethers), poly(esters), simple hydrocarbons, and simple hydrocarbons containing functionalities such as carbonyl, carboxyl, amide, carbamate, urea, or ether. These types of resins are commercially available and can be obtained, for example, from National Starch and Chemical Company and Dainippon Ink and Chemical, Inc.

Specific preferred maleimide resins include

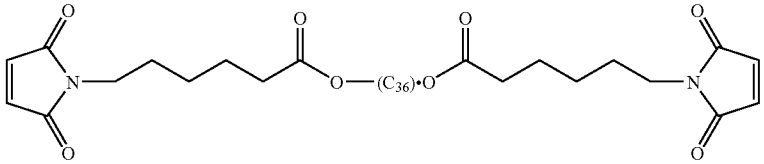

in which $C_{36}$ represents a linear or branched chain (with or without cyclic moieties) of 36 carbon atoms;

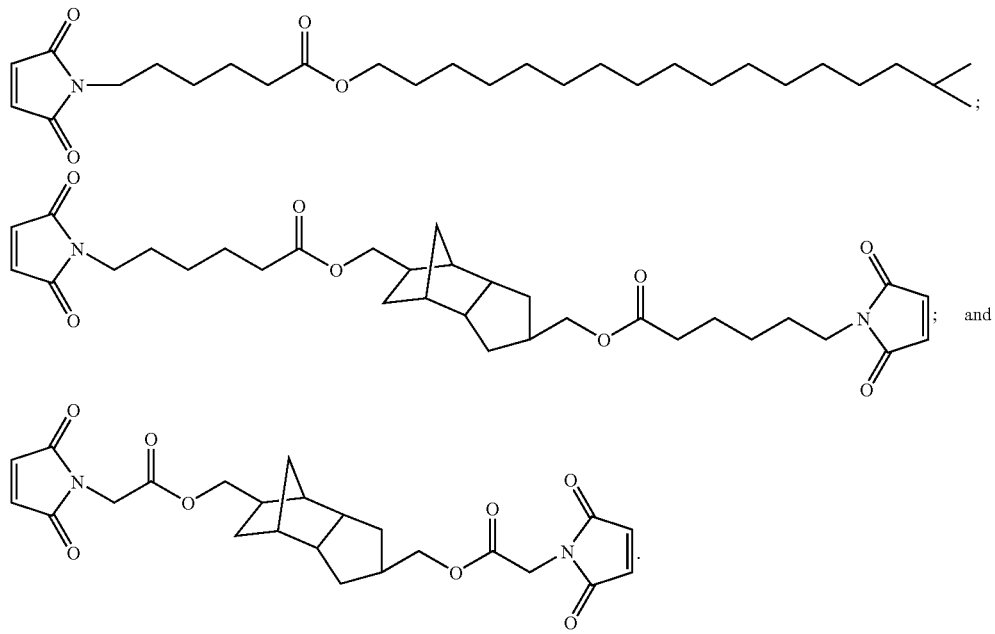

Suitable acrylate resins for use in formulation with the inventive oligomers include those having the generic structure

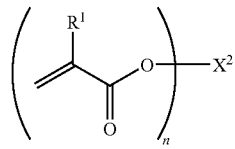

in which n is 1 to 6, $R^1$ is —H or —$CH_3$, and $X^2$ is an aromatic or aliphatic group. Exemplary $X^2$ entities include poly(butadienes), poly(carbonates), poly(urethanes), poly(ethers), poly(esters), simple hydrocarbons, and simple hydrocarbons containing functionalities such as carbonyl, carboxyl, amide, carbamate, urea, or ether. Commercially available materials include butyl(meth)acrylate, isobutyl(meth)acrylate, 2-ethyl hexyl(meth)acrylate, isodecyl(meth)acrylate, n-lauryl(meth) acrylate, alkyl(meth)acrylate, tridecyl(meth)acrylate, n-stearyl(meth)acrylate, cyclohexyl(meth)acrylate, tetrahydrofurfuryl(meth)acrylate, 2-phenoxy ethyl(meth)acrylate, isobornyl(meth)acrylate, 1,4-butanediol di(meth)acrylate, 1.6 hexanediol di(meth)acrylate, 1,9-nonandiol di(meth) acrylate, perfluorooctylethyl(meth)acrylate, 1,10 decandiol di(meth)acrylate, nonylphenol polypropoxylate (meth)acrylate, and polypentoxylate tetrahydrofurfuryl acrylate, available from Kyoeisha Chemical Co., LTD; polybutadiene urethane dimethacrylate (CN302, NTX6513) and polybutadiene dimethacrylate (CN301, NTX6039, PRO6270) available from Sartomer Company, Inc; polycarbonate urethane diacrylate (ArtResin UN9200A) available from Negami Chemical Industries Co., LTD; acrylated aliphatic urethane oligomers (Ebecryl 230, 264, 265, 270, 284, 4830, 4833, 4834, 4835, 4866, 4881, 4883, 8402, 8800-20R, 8803, 8804) available from Radcure Specialities, Inc; polyester acrylate oligomers (Ebecryl 657, 770, 810, 830, 1657, 1810, 1830) available from Radcure Specialities, Inc.; and epoxy acrylate resins (CN104, 111, 112, 115, 116, 117, 118, 119, 120, 124, 136) available from Sartomer Company, Inc. In one embodiment the acrylate resins are selected from the group consisting of isobornyl acrylate, isobornyl methacrylate, lauryl acrylate, lauryl methacrylate, poly(butadiene) with acrylate functionality and poly(butadiene) with methacrylate functionality.

Suitable vinyl ether resins for use in formulations with the inventive oligomers include those having the generic structure

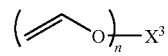

in which n is 1 to 6 and $X^3$ is an aromatic or aliphatic group. Exemplary $X^3$ entities include poly(butadienes), poly(carbonates), poly(urethanes), poly(ethers), poly(esters), simple hydrocarbons, and simple hydrocarbons containing functionalities such as carbonyl, carboxyl, amide, carbamate, urea, or ether. Commercially available resins include cyclohenanedimethanol divinylether, dodecylvinylether, cyclohexyl vinylether, 2-ethylhexyl vinylether, dipropyleneglycol divinylether, hexanediol divinylether, octadecylvinylether, and butandiol divinylether available from International Speciality Products (ISP); Vectomer 4010, 4020, 4030, 4040, 4051, 4210, 4220, 4230, 4060, 5015 available from Sigma-Aldrich, Inc.

Suitable poly(butadiene) resins for use in formulations with the inventive oligomers include poly(butadienes), epoxidized poly(butadienes), maleic poly(butadienes), acrylated poly(butadienes), butadiene-styrene copolymers, and butadiene-acrylonitrile copolymers. Commercially available materials include homopolymer butadiene (Ricon 130, 131, 134, 142, 150, 152, 153, 154, 156, 157, P30D) available from Sartomer Company, Inc; random copolymer of butadiene and styrene (Ricon 100, 181, 184) available from Sartomer Company Inc.; maleinized poly(butadiene) (Ricon 130MA8, 130MA13, 130MA20, 131MA5, 131MA10, 131MA17, 131MA20, 156MA17) available from Sartomer Company, Inc.; acrylated poly(butadienes) (CN302, NTX6513, CN301, NTX6039, PRO6270, Ricacryl 3100, Ricacryl 3500) available from Sartomer Inc.; epoxydized poly(butadienes) (Polybd 600, 605) available from Sartomer Company. Inc. and Epolead PB3600 available from Daicel Chemical Industries, Ltd; and acrylonitrile and butadiene copolymers (Hycar CTBN series, ATBN series, VTBN series and ETBN series) available from Hanse Chemical.

Suitable epoxy resins for use in formulations containing the inventive oligomers include bisphenol, naphthalene, and aliphatic type epoxies. Commercially available materials include bisphenol type epoxy resins (Epiclon 830LVP, 830CRP, 835LV, 850CRP) available from Dainippon Ink & Chemicals, Inc.; naphthalene type epoxy (Epiclon HP4032) available from Dainippon Ink & Chemicals, Inc.; aliphatic epoxy resins (Araldite CY179, 184, 192, 175, 179) available from Ciba Specialty Chemicals, (Epoxy 1234, 249, 206) available from Union Carbide Corporation, and (EHPE-3150) available from Daicel Chemical Industries, Ltd. Other suitable epoxy resins include cycloaliphatic epoxy resins, bisphenol-A type epoxy resins, bisphenol-F type epoxy resins, epoxy novolac resins, biphenyl type epoxy resins, naphthalene type epoxy resins, dicyclopentadiene-phenol type epoxy resins, reactive epoxy diluents, and mixtures thereof.

Suitable siliconized olefin resins for use in the formulations containing the inventive oligomers are obtained by the selective hydrosilation reaction of silicone and divinyl materials, having the generic structure,

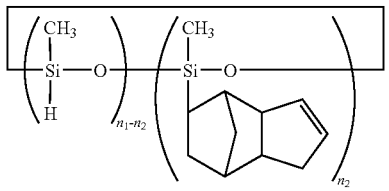

in which $n_1$ is 2 or more, $n_2$ is 1 or more and $n_1 > n_2$. These materials are commercially available and can be obtained, for example, from National Starch and Chemical Company.

Suitable silicone resins for use in formulations with the inventive oligomers include reactive silicone resins having the generic structure

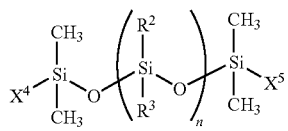

in which n is 0 or any integer, $X^4$ and $X^5$ are hydrogen, methyl, amine, epoxy, carboxyl, hydroxy, acrylate, methacrylate, mercapto, phenol, or vinyl functional groups, $R^2$ and $R^3$ can be —H, —CH$_3$, vinyl, phenyl, or any hydrocarbon structure with more than two carbons. Commercially available materials include KF8012, KF8002, KF8003, KF1001, X-22-3710, KF6001, X-22-164C, KF2001, X-22-170DX, X-22-173DX, X-22-174DX X-22-176DX, KF-857, KF862, KF8001, X-22-3367, and X-22-3939A available from Shin-Etsu Silicone International Trading (Shanghai) Co., Ltd.

Suitable styrene resins for use in formulations with the inventive oligomers include those resins having the generic structure

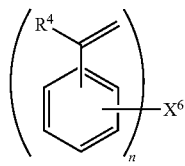

in which n is 1 or greater, $R^4$ is —H or —CH$_3$, and $X^6$ is an aliphatic group. Exemplary $X^3$ entities include poly(butadienes), poly(carbonates), poly(urethanes), poly(ethers), poly(esters), simple hydrocarbons, and simple hydrocarbons containing functionalities such as carbonyl, carboxyl, amide, carbamate, urea, or ether. These resins are commercially available and can be obtained, for example, from National Starch and Chemical Company or Sigma-Aldrich Co.

Suitable cyanate ester resins for use in formulations with the inventive oligomers include those having the generic structure

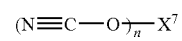

in which n is 1 or larger, and $X^7$ is a hydrocarbon group. Exemplary $X^7$ entities include bisphenol, phenol or cresol novolac, dicyclopentadiene, polybutadiene, polycarbonate, polyurethane, polyether, or polyester. Commercially available materials include; AroCy L-10, AroCy XU366, AroCy XU371, AroCy XU378, XU71787.02L, and XU 71787.07L, available from Huntsman LLC; Primaset PT30, Primaset PT30 S75, Primaset PT60, Primaset PT60S, Primaset BADCY, Primaset DA230S, Primaset MethylCy, and Primaset LECY, available from Lonza Group Limited; 2-allyphenol cyanate ester, 4-methoxyphenol cyanate ester, 2,2-bis(4-cyanatophenol)-1,1,1,3,3,3-hexafluoropropane, bisphenol A cyanate ester, diallylbisphenol A cyanate ester, 4-phenylphenol cyanate ester, 1,1,1-tris(4-cyanatophenyl) ethane, 4-cumylphenol cyanate ester, 1,1-bis(4-cyanateophenyl)ethane, 2,2,3,4,4,5,5,6,6,7,7-dodecafluorooctanediol dicyanate ester, and 4,4'-bisphenol cyanate ester, available from Oakwood Products, Inc.

Additional polymers suitable for use in formulations with the inventive oligomers include polyamide, phenoxy, polybenzoxazine, polyether sulfone, polyimide, benzoxazine, vinyl ether, polyolefin, polybenzoxyzole, polyester, polystyrene, polycarbonate, polypropylene, poly(vinyl chloride), polyisobutylene, polyacrylonitrile, poly(methyl methacrylate), poly(vinyl acetate), poly(2-vinylpridine), cis-1,4-polyisoprene, 3,4-polychloroprene, vinyl copolymer, poly(ethylene oxide), poly(ethylene glycol), polyformaldehyde, polyacetaldehyde, poly(b-propiolacetone), poly(10-decanoate), poly(ethylene terephthalate), polycaprolactam, poly(11-undecanoamide), poly(m-phenylene-terephthalamide), poly(tetramethlyene-m-benzenesulfonamide), polyester polyarylate, poly(phenylene oxide), poly(phenylene sulfide), polysulfone, polyimide, polyetheretherketone, polyetherimide, fluorinated polyimide, polyimide siloxane, polyiosindolo-quinazolinedione, polythioetherimide poly-phenyl-quinoxaline, polyquuinixalone, imide-aryl ether phenylquinoxaline copolymer, polyquinoxaline, polybenzimidazole, polybenzoxazole, polynorbornene, poly(arylene ethers), polysilane, parylene, benzocyclobutenes, hydroxy (benzoxazole) copolymer, poly(silarylene siloxanes), and polybenzimidazole.

Other suitable materials for inclusion in adhesive, coating, and encapsulant compositions containing the inventive oligomers include rubber polymers such as block copolymers of monovinyl aromatic hydrocarbons and conjugated diene, e.g., styrene-butadiene, styrene-butadiene-styrene (SBS), styrene-isoprene-styrene (SIS), styrene-ethylene-butylene-styrene (SEBS), and styrene-ethylene-propylene-styrene (SEPS).

Other suitable materials for inclusion in compositions containing the inventive oligomers include ethylene-vinyl acetate polymers, other ethylene esters and copolymers, e.g., ethylene methacrylate, ethylene n-butyl acrylate and ethylene acrylic acid; polyolefins such as polyethylene and polypropylene; polyvinyl acetate and random copolymers thereof; polyacrylates; polyamides; polyesters; and polyvinyl alcohols and copolymers thereof.

Suitable thermoplastic rubbers for use in formulations containing the inventive oligomers include carboxy terminated butadiene-nitrile (CTBN)/epoxy adduct, acrylate rubber, vinyl-terminated butadiene rubber, and nitrile butadiene rubber (NBR). In one embodiment the CTBN epoxy adduct consists of about 20-80 wt % CTBN and about 20-80 wt % diglycidyl ether bisphenol A: bisphenol A epoxy (DGEBA). A variety of CTBN materials are available from Noveon Inc., and a variety of bisphenol A epoxy materials are available from Dainippon Ink and Chemicals, Inc., and Shell Chemicals. NBR rubbers are commercially available from Zeon Corporation.

Suitable siloxanes for use in formulations containing the inventive oligomers include elastomeric polymers comprising a backbone and pendant from the backbone at least one siloxane moiety that imparts permeability, and at least one reactive moiety capable of reacting to form a new covalent bond. Examples of suitable siloxanes include elastomeric polymers prepared from: 3-(tris(trimethyl-silyloxy)silyl)-propyl methacrylate, n-butyl acrylate, glycidyl methacrylate, acrylonitrile, and cyanoethyl acrylate; 3-(tris(trimethylsilyloxy)silyl)-propyl methacrylate, n-butyl acrylate, glycidyl methacrylate, and acrylonitrile; and 3-(tris(trimethylsilyloxy)silyl)-propyl methacrylate, n-butyl acrylate, glycidyl methacrylate, and cyanoethyl acrylate.

If a curing agent is required, its selection is dependent on the polymer chemistry used and the processing conditions employed. As curing agents, the compositions may use aromatic amines, alycyclic amines, aliphatic amines, tertiary phosphines, triazines, metal salts, aromatic hydroxyl compounds, or a combination of these. Appropriateness of the type and amount of catalyst used for specific compositions is disclosed in the open literature and is within the expertise of one skilled in the art.

Examples of such catalysts include imidazoles, such as 2-methylimidazole, 2-undecylimidazole, 2-heptadecyl imidazole, 2-phenylimidazole, 2-ethyl 4-methylimidazole, 1-benzyl-2-methylimidazole, 1-propyl-2-methylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, 1-guanaminoethyl-2-methylimidazole and addition product of an imidazole and trimellitic acid; tertiary amines, such as N,N-dimethyl benzylamine, N,N-dimethylaniline, N,N-dimethyltoluidine, N,N-dimethyl-p-anisidine, p-halogeno-N,N-dimethylaniline, 2-N-ethylanilino ethanol, tri-n-butylamine, pyridine, quinoline, N-methylmorpholine, triethanolamine, triethylenediamine, N,N,N',N'-tetramethylbutanediamine, N-methylpiperidine; phenols, such as phenol, cresol, xylenol, resorcine, and phloroglucin; organic metal salts, such as lead naphthenate, lead stearate, zinc naphthenate, zinc octolate, tin oleate, dibutyl tin maleate, manganese naphthenate, cobalt naphthenate, and acetyl aceton iron; and inorganic metal salts, such as stannic chloride, zinc chloride and aluminum chloride; peroxides, such as benzoyl peroxide, lauroyl peroxide, octanoyl peroxide, acetyl peroxide, para-chlorobenzoyl peroxide and di-t-butyl diperphthalate; acid anhydrides, such as carboxylic acid anhydride, maleic anhydride, phthalic anhydride, lauric anhydride, pyromellitic anhydride, trimellitic anhydride, hexahydrophthalic anhydride; hexahydropyromellitic anhydride and hexahydrotrimellitic anhydride, azo compounds, such as azoisobutylonitrile, 2,2'-azobispropane, m,m'-azoxystyrene, hydrozones, and mixtures thereof.

Suitable curing accelerators may be selected from the group consisting of triphenylphosphine, alkyl-substituted imidazoles, imidazolium salts, onium salts, quartenary phosphonium compounds, onium borates, metal chelates, 1,8-diazacyclo[5.4.0]undex-7-ene or a mixture thereof.

The curing agent can be either a free radical initiator or cationic initiator, depending on whether a radical or ionic curing resin is chosen. If a free radical initiator is used, it will be present in an effective amount. An effective amount typically is 0.1 to 10 percent by weight of the organic compounds (excluding any filler). Appropriate free-radical initiators include peroxides, such as butyl peroctoates and dicumyl peroxide, and azo compounds, such as 2,2'-azobis(2-methyl-propanenitrile) and 2,2'-azobis(2-methyl-butanenitrile). Preferred cationic curing agents include dicyandiamide, phenol novolak, adipic dihydrazide, diallyl melamine, diamino malconitrile, BF3-amine complexes, amine salts and modified imidazole compounds.

Metal compounds also can be employed as cure accelerators for cyanate ester systems and include, but are not limited to, metal napthenates, metal acetylacetonates (chelates), metal octoates, metal acetates, metal halides, metal imidazole complexes, and metal amine complexes. Other cure accelerators that may be included in the coating formulation include triphenylphosphine, alkyl-substituted imidazoles, imidazolium salts, and onium borates In some cases, it may be desirable to use more than one type of cure. For example, both cationic and free radical initiation may be desirable, in which case both free radical cure and ionic cure resins can be used in the composition. These compositions would contain effective amounts of initiators for each type of resin. Such a composition would permit, for example, the curing process to be started by cationic initiation using UV irradiation, and in a later processing step, to be completed by free radical initiation upon the application of heat.

If the coating material contains solvent it will typically require a drying and/or B-staging step. As used herein, "B-staging" (and its variants) is used to refer to the processing of a material by heat or irradiation so that if the material is solubilized or dispersed in a solvent, the solvent is evaporated off with or without partial curing of the material, or if the material is neat with no solvent, the material is partially cured to a tacky or more hardened state. For example, if the material is a flow-able adhesive, B-staging will provide extremely low flow without fully curing, such that additional curing may be performed after the adhesive is used to join one article to another. The reduction in flow may be accomplished by evaporation of a solvent, partial advancement or curing of a resin or polymer, or both. The time and temperature required to achieve this will vary according to the solvent and composition used and can be determined by the practitioner without undue experimentation. The drying and/or B-staging may be done as a step separate from the curing of the end use composition, or it may be done as a separate process step.

If the composition does not contain solvent it may still be desirable to B-stage, or partially advance, the material. This may be done prior to cure to effect hardening of the coating to a non-tacky state so that additional processing may be done before the coating is fully cured.

The coating may or may not require curing, depending on the purpose and composition of the coating. If the coating does require curing, the cure may be accomplished either as an individual process step, or in conjunction with another processing operation. An example of another processing operation is solder reflow, which is a step in the manufacture of certain semiconductor devices.

Within the manufacturing steps for semiconductors, coatings are applied to the silicon dies used as semiconductors or microprocessors. The coatings can be applied either on the silicon wafer before it is singulated into individual dies, or on the individual dies themselves. For example, therefore, the cure may be done at the wafer level or at the die level, depending on the purpose of the coating, the composition of the coating, and the manufacturing process employed.

If a curing step is utilized, the cure temperature will generally be within a range of 80°-250° C., and curing will be effected within a time period ranging from few seconds or up to 120 minutes, depending on the particular resin chemistry and curing agents chosen. The time and temperature curing profile for each composition will vary, and different compositions can be designed to provide the curing profile that will be suited to the particular industrial manufacturing process.

Depending on the end application, one or more fillers may be included in the composition and usually are added for improved rheological properties and stress reduction. Examples of suitable nonconductive fillers include alumina, aluminum hydroxide, silica, vermiculite, mica, wollastonite, calcium carbonate, titania, sand, glass, barium sulfate, zirconium, carbon black, organic fillers, and halogenated ethylene polymers, such as, tetrafluoroethylene, trifluoroethylene, vinylidene fluoride, vinyl fluoride, vinylidene chloride, and vinyl chloride. Exemplary electrically or thermally conductive fillers include carbon black, graphite, gold, silver, copper, platinum, palladium, nickel, aluminum, silicon carbide, boron nitride, diamond, and alumina.

The filler particles may be of any appropriate size ranging from nano size to several mm. The choice of such size for any particular end use is within the expertise of one skilled in the art. When used in a formulation, fillers typically are present in an amount from 0 to 95%, preferably 20 to 85%, by weight of the total composition.

It is desirable for some compositions to add a fluxing agent to remove metal oxides and prevent re-oxidation of electrical solder joints or of metallic substrates. Fluxing agent selection will depend on the resin chemistry and metallurgy presented. Some of the key requirements of the fluxing agent are that it, and fluxing residues generated by the fluxing process, should not affect the curing of the oligomers or resins present in the composition, should not be too corrosive, and should not out-gas to a detrimental level during heating cycles.

Examples of suitable fluxing agents include compounds that contain one or more hydroxyl groups (—OH), or carboxylic (—COOH) groups or both, such as are present in organic carboxylic acids, anhydrides, and alcohols. Exemplary fluxing agents are, for example, rosin gum, dodecanedioic acid (commercially available as Corfree M2 from Aldrich), sebasic acid, polysebasic polyanhydride, maleic acid, hexahydrophthalic anhydride, methyl hexahydrophthalic anhydride, ethylene glycol, glycerin, tartaric acid, adipic acid, citric acid, malic acid, glutaric acid, glycerol, 3-[bis(glycidyl oxy methyl)methoxy]-1,2-propane diol, D-ribose, D-cellobiose, cellulose, 3-cyclohexene-I,1-dimethanol; amine fluxing agents, such as, aliphatic amines having 1 to 10 carbon atoms, e.g., trimethylamine, triethylamine, n-propylamine, n-butylamine, isobutylamine, sec-butylamine, t-butylamine, n-amylamine, sec-amylamine, 2-ethylbutylamine, n-heptylamine, 2-ethylhexylamine, n-octylamine, and t-octylamine; epoxy resins employing a cross-linking agent with fluxing properties. Fluxing agents may also be compounds that chelate with a metal substrate. Fluxing agents will be present in an effective amount, and typically an effective amount ranges from 1 to 30% by weight.

In some compositions it may be desirable to add a coupling agent to the composition. Suitable coupling agents are epoxy silanes, amine silanes agent, or mercapto silanes. Coupling agents, if used, will be used in an effective amount, and a typical effective amount is an amount up to 5% by weight.

For some applications, the composition may also contain a surfactant. Suitable surfactants include organic acrylic polymers, silicones, polyethylene glycol, polyoxyethylene/polyoxypropylene block copolymers, ethylene diamine based polyoxyethylene/polyoxypropylene block copolymers, polyol-based polyoxyalkylenes, fatty alcohol-based polyoxyalkylenes, fatty alcohol polyoxyalkylene alkyl ethers, and mixtures thereof. Surfactants, if used, will be used in an effective amount, and a typical effective amount is an amount up to 5% by weight.

Wetting agents also may be included in the composition. Wetting agent selection will depend on the application requirements and the resin chemistry utilized. Wetting agents, if used, will be used in an effective amount and a typical effective amount is up to 5% by weight. Examples of suitable wetting agents include Fluorad FC-4430 Fluorosurfactant available from 3M, Clariant Fluowet OTN, BYK W-990, Surfynol 104 Surfactant, Crompton Silwet L-7280, Triton X100 available from Rhom and Haas, Propylene glycol with a preferable Mw greater than 240, Gama-Butyrolactone, castor oil, glycerin or other fatty acids, and silanes.

A flow control agent also may be included in the composition. Flow control agent selection will depend on the application requirements and resin chemistry employed. Flow control agents, if used, will be present in an effective amount: an effective amount is an amount up to 5% by weight. Examples of suitable flow control agents include Cab-O-Sil TS720 available from Cabot, Aerosil R202 or R972 available from Degussa, fumed silicas, fumed aluminas, or fumed metal oxides.

Some compositions may include an adhesion promoter, and selection of an appropriate adhesion promoter will depend on the application requirements and resin chemistry employed. Adhesion promoters, if used, will be used in an effective amount and an effective amount is an amount up to 5% by weight. Examples of suitable adhesion promoters include: silane coupling agents such as Z6040 epoxy silane or Z6020 amine silane available from Dow Corning; A186 Silane, A187 Silane, A174 Silane, or A1289 available from OSI Silquest; Organosilane SI264 available from Degussa; Johoku Chemical CBT-1 Carbobenzotriazole available from Johoku Chemical; functional benzotriazoles; thiazoles; titanates; and zirconates.

An air release agent (defoamer) is another optional component to the composition. Air release agent selection will depend on the application requirements and resin chemistry employed. Air release agents, if used, will be used in an effective amount and an effective amount will be an amount up to 5% by weight. Examples of suitable air release agents include Antifoam 1400 available from Dow Corning, DuPont Modoflow, and BYK A-510.

In some embodiments these compositions are formulated with tackifying resins in order to improve adhesion and introduce tack; examples of tackifying resins include naturally-occurring resins and modified naturally-occurring resins; polyterpene resins; phenolic modified terpene resins; coumarons-indene resins; aliphatic and aromatic petroleum hydrocarbon resins; phthalate esters; hydrogenated hydrocarbons, hydrogenated rosins and hydrogenated rosin esters.

In some embodiments other components may be included, for example, diluents such as liquid polybutene or polypropylene; petroleum waxes such as paraffin and microcrystalline waxes, polyethylene greases, hydrogenated animal, fish and vegetable fats, mineral oil and synthetic waxes, naphthenic or paraffinic mineral oils.

In other embodiments, monofunctional reactive diluents can be included to incrementally delay an increase in viscosity without adversely affecting the physical properties of the cured coating. Suitable diluents include p-tert-butyl-phenyl glycidyl ether, allyl glycidyl ether, glycerol diblycidyl ether, glycidyl ether of alkyl phenol (commercially available from Cardolite Corporation as Cardolite NC513), and Butanedio-diglycidylether (commercially available as BDGE from Aldrich). Preferred diluents are the reactive diluents disclosed earlier in this specification.

Other additives, such as stabilizers, antioxidants, impact modifiers, and colorants, in types and amounts known in the art, may also be added to the formulation.

Common solvents that readily dissolve the resins, and with a proper boiling point ranging from 25° C. to 200° C. can be used for various applications. Examples of solvents that may be utilized include ketones, esters, alcohols, ethers, and other common solvents that are stable. Suitable solvents include γ-butyrolactone, propylene glycol methyl ethyl acetate (PG-MEA), and 4-methyl-2-pentanone.

Curing can take place by thermal exposure, ultraviolet (UV) or microwave irradiation, or a combination of these. Curing conditions will be tailored to the specific formulation and can be readily determined by the practitioner. Furthermore, the composition may be B-stageable or not, depending on the application requirements.

EXAMPLES

Example 1

Preparation of Imide-Alcohol from 4,4'(Hexafluoro-isopropylidine)Bisphthalic Anhydride (6FDA) and 4-Aminophenethyl Alcohol 4-Aminophenethyl alcohol (20.0 grams, 0.1458 mol) was added (generation of an exotherm was not observed on this scale). All solids dissolved forming a dark brown solution. 6FDA (29.4 grams, 0.0663 mol) was added over five minutes, and with this addition a slight temperature increase (<10° C.) was noted. The dark gold-brown reaction was mixed for one hour at room temperature. The reaction flask was fitted with a Dean-Stark trap and condenser, placed in a hot oil bath (preheated to 145° C.) and heated at reflux for 11 hours. During the reaction nearly all theoretical water generated by the reaction was collected in the trap. After heating, the reaction was cooled to room temperature, placed in a separatory funnel and allowed to phase-out. The top colorless phase was separated from the dark-brown bottom phase and discarded. The dark brown phase was dissolved in 500 mL of dichloromethane and washed twice in a separatory funnel with 500 mL of 5% hydrogen chloride solution. These washes serve to protonate and remove residual/excess 4-aminophenethyl alcohol. The efficiency of these washes can be monitored by TLC eluting in a 5/1 (volume) acetone/methanol solvent system. The acid washes were then followed by a distilled water wash of 500 mL. Following the washes, the bottom organic phase was collected as a hazy gold solution and dried over 40 grams of magnesium sulfate. Filtration resulted in a clear gold reaction solution. Solvent was stripped from the solution on a roto-evaporator at 40° C. leaving 34 grams of a yellow crystalline solid, a yield of 79%. The identity of the product was confirmed using $^1$H-NMR, see FIG. 1.

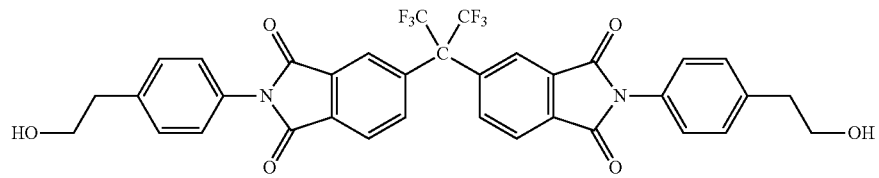

Example 2

Preparation of Imide-Alcohol from 4,4'-Bisphenol-A Dianhydride and 4-Aminophenethyl Alcohol

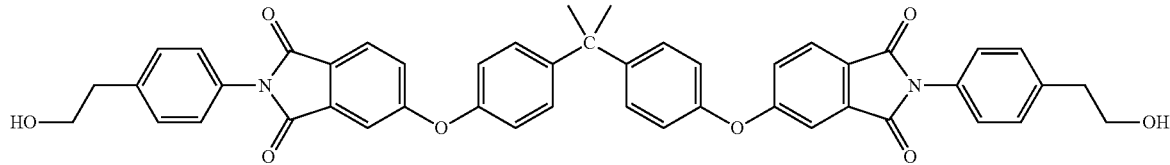

Triethylamine (47.0 grams, 0.4641 mol) and toluene (260 mL) were combined in a one liter (1 L) 4-neck round-bottom reaction flask equipped with a thermometer and mechanical mixer. Methanesulfonic acid (45.8 grams, 0.4772 mol) was slowly added with moderate mixing. An exotherm was generated but a temperature of <45° C. was maintained by controlling the rate of addition. The addition was completed within one hour. After the addition, the reaction appeared as a colorless hazy solution and was mixed for ten minutes.

Triethylamine (58.6 grams, 0.5796 mol) and toluene (300 mL) were combined in a 1 L 4-neck round-bottom reaction flask equipped with a thermometer and mechanical mixer. Methanesulfonic acid (57.3 grams, 0.5962 mol) was slowly added with moderate mixing. An exotherm was generated but a temperature of <45° C. was maintained by controlling the rate of addition. The addition was completed within one hour. After the addition, the reaction appeared as a colorless hazy solution and was mixed for ten minutes. 4-Aminophenethyl alcohol (25.0 grams, 0.1822 mol) was added (generation of an exotherm was not observed on this scale). Within 20 minutes, all solids dissolved forming a dark brown solution. 4,4'-Bisphenol A dianhydride (43.1 grams, 0.0828 mol) was added over five minutes. The dark gold-brown reaction mixture was stirred for one hour at room temperature (no exotherm was noted). The reaction flask was fitted with a Dean-Stark trap and condenser, placed in a hot oil bath (preheated to 145° C.) and mixed/heated at reflux for 12 hours. Note that within the first 30 minutes of heating, all solids dissolved. During the reaction nearly all theoretical water generated by the reaction was collected in the trap. After heating, the reaction was cooled to room temperature, placed in a separatory funnel and allowed to phase-out. The top colorless phase was separated from the dark-brown bottom phase and discarded. The dark brown phase was dissolved in 250 mL of dichloromethane and washed twice in the separatory funnel with 500 mL of 5% hydrogen chloride solution. These washes serve to protonate and remove residual/excess 4-aminophenethyl alcohol. The efficiency of these washes can be monitored by TLC eluting in a 5/1 (volume) acetone/methanol solvent system. The acid washes were followed by a distilled water wash of 500 mL. Following the washes, the bottom organic phase was collected as a hazy gold-brown solution, which was dried over 40 grams of magnesium sulfate. Filtration resulted in a clear amber reaction solution. Solvent was stripped from the solution on a roto-evaporator at 40° C. leaving 45 grams of a tan crystalline solid, a yield of 71%.

The identity of the product was confirmed using 1H-NMR, see FIG. 2.

Example 3

Preparation of Oligomer from Intermediate of Example 1 and Maleimidocaproic Acid (MCA)

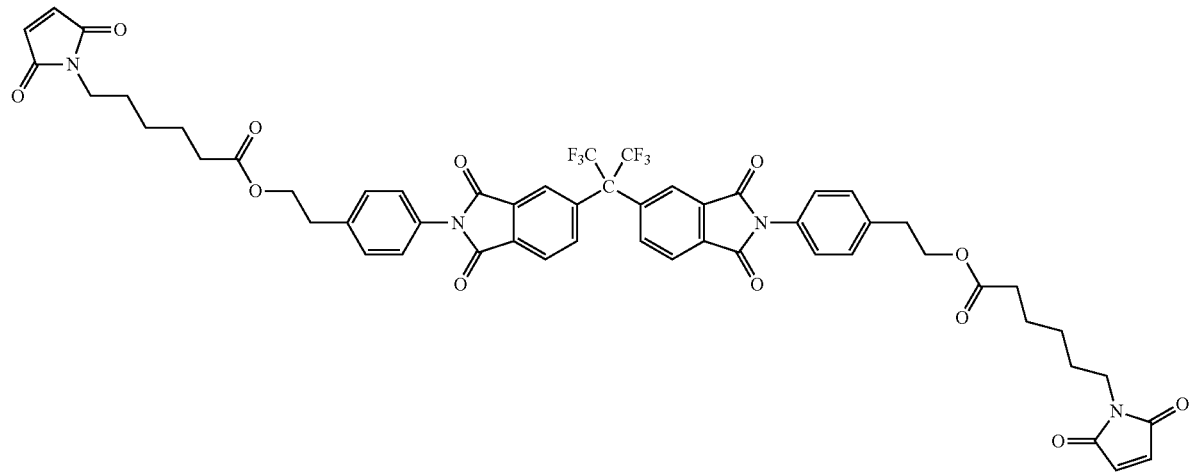

MCA (14.2 grams, 0.0673 mol), intermediate from Example 1 (20.0 grams, 0.0306 mol), and toluene (100 mL) were charged to a 250 mL 4-neck round-bottom reaction flask equipped with a thermometer, mechanical mixer, condenser and Dean-Stark trap. The reaction flask was purged with nitrogen while mixing at 300 rpms in a hot oil bath preheated to 140° C. When the reaction temperature reached 80°-90° C., all solids were dissolved and sulfuric acid (0.30 grams) was carefully added. Shortly thereafter, the reaction started refluxing at 112° C. The nitrogen purge was removed and the reaction maintained at reflux temperature with mixing for ten hours. The reaction was monitored by measuring water volume generated and collected in the Dean Stark trap vs. theoretical (1.1 mL). During the reaction, some gel formed on the flask sides, the color of the reaction solution changed from clear yellow-orange to clear gold-brown, and 0.8 mL of water was collected in the Dean-Stark trap. The reaction was filtered resulting in a clear dark copper solution. An exchange resin (20 grams) was added and the mixture was stirred mechanically for one hour. Following filtration of the exchange resin, 20 grams of silica gel was added and the mixture stirred mechanically for one hour. The silica gel was filtered out, the golden reaction solution stripped of solvent on the roto-evaporator, and the resulting light crystalline solid pulverized and dried in a vacuum oven at 60° C. The structure was confirmed by 1H-NMR, see FIG. 3. As was typical of most MCA derivatives, Michael adducts are the bulk of the impurities in this material. The mp of the oligomeric product was measured at 45° C. by Fisher mp apparatus.

Example 4

Preparation of Oligomer from Intermediate from Example 2 and MCA

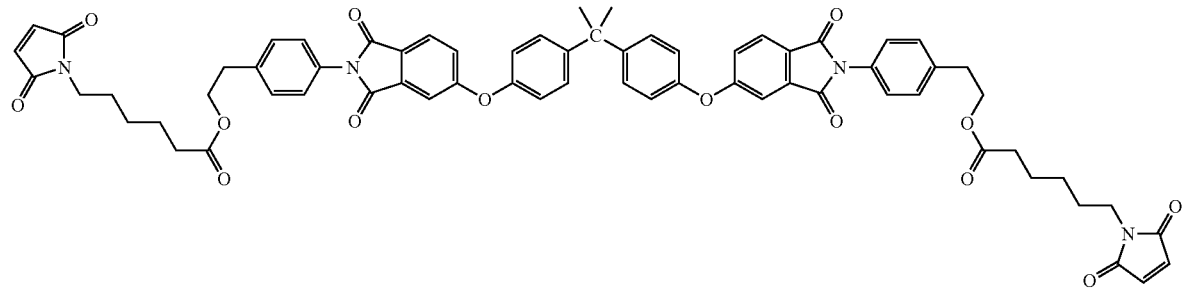

MCA (24.45 grams, 0.1159 mol), intermediate from Example 2 (40.0 grams, 0.0527 mol) and toluene (200 mL) were charged to a 500 mL 4-neck round-bottom reaction flask equipped with a thermometer, mechanical mixer, condenser and Dean-Stark trap. The reaction flask was purged with nitrogen while mixing at 300 rpms in a hot oil bath preheated to 140° C. When the reaction temperature reached 80°-90° C., all solids were dissolved and sulfuric acid (0.49 grams) was added. Shortly thereafter, the reaction started refluxing at 112° C. The nitrogen purge was removed and the reaction maintained at reflux temperature with mixing for ten hours. The reaction was monitored by measuring water volume generated and collected in the Dean Stark trap vs. theoretical (1.9 mL). During the reaction, gel formed on the flask sides, the color of the reaction solution changed from hazy gold to clear copper, and 1.9 mL of water was collected in the Dean-Stark trap. The reaction was filtered resulting in a clear dark copper solution. An exchange resin (40 grams) was added and the mixture was stirred mechanically for one hour. During filtration of the exchange resin, flocculant appeared in the solution. The volume of the solution was increased to 800 mL with the addition of toluene, the solution was filtered, and the filtration resulted in a hazy gold solution. Silica gel (40 grams) was added and the mixture stirred mechanically for one hour. The silica gel was filtered out to leave a clear yellow solution, which was stripped of solvent on the roto-evaporator. The resulting light crystalline solid was pulverized and dried in a vacuum oven at 60° C. The structure was confirmed by 1H-NMR, see FIG. 4. As was typical of most MCA derivatives, Michael adducts are the bulk of the impurities in this material. The mp of the oligomeric product was measured at 41° C. by Fisher mp apparatus.

Example 5

Preparation of Oligomer from Intermediate from Example 2, MCA, and Methacrylic Acid

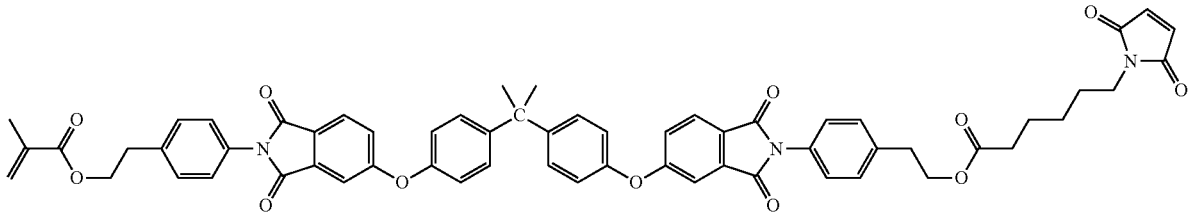

MCA (12.24 grams, 0.0580 mol), methacrylic acid (5.00 grams, 0.0580 mol), intermediate from Example 2 (40.0 grams, 0.0527 mol), and toluene (200 mL) were charged to a 500 mL 4-neck round-bottom reaction flask equipped with a thermometer, mechanical mixer, condenser and Dean-Stark trap. The reaction flask was purged with nitrogen while mixing at 300 rpms in a hot oil bath preheated to 140° C. When the reaction temperature reached 80°-90° C., all solids were dissolved and sulfuric acid (0.49 grams) was carefully added. Shortly thereafter, the reaction started refluxing at 112° C. The nitrogen purge was then removed and the reaction maintained at reflux with mixing for ten hours. The reaction was monitored by measuring water volume generated and collected in the Dean Stark trap vs. theoretical (1.9 mL). During the reaction, some gel formed on the flask sides, the color of the reaction solution changed from hazy brown gold to dark cloudy copper and water was collected in the Dean-Stark trap. Upon completion, the reaction was hot-filtered resulting in a clear dark copper solution. An exchange resin (34 grams) was added and the mixture stirred mechanically for one hour. The reaction mixture was filtered resulting in a hazy deep yellow solution. A residual light gold coating was noted on the flask sides and the exchange resin formed sticky clumps upon filtration. Silica gel (34 grams) was then added to the reaction solution and the mixture stirred mechanically for one hour. The silica gel was filtered out and 0.03 grams of methyl hydroquinone added as a polymerization inhibitor. The resulting clear yellow reaction solution was stripped of solvent on a roto-evaporator at 40° C. yielding an amorphous yellow solid upon cooling. Product structure was confirmed by $^1$HNMR, see FIG. 5.

Example 6

Preparation of Oligomer from Intermediate from Example 2, Dimer Acid and MCA

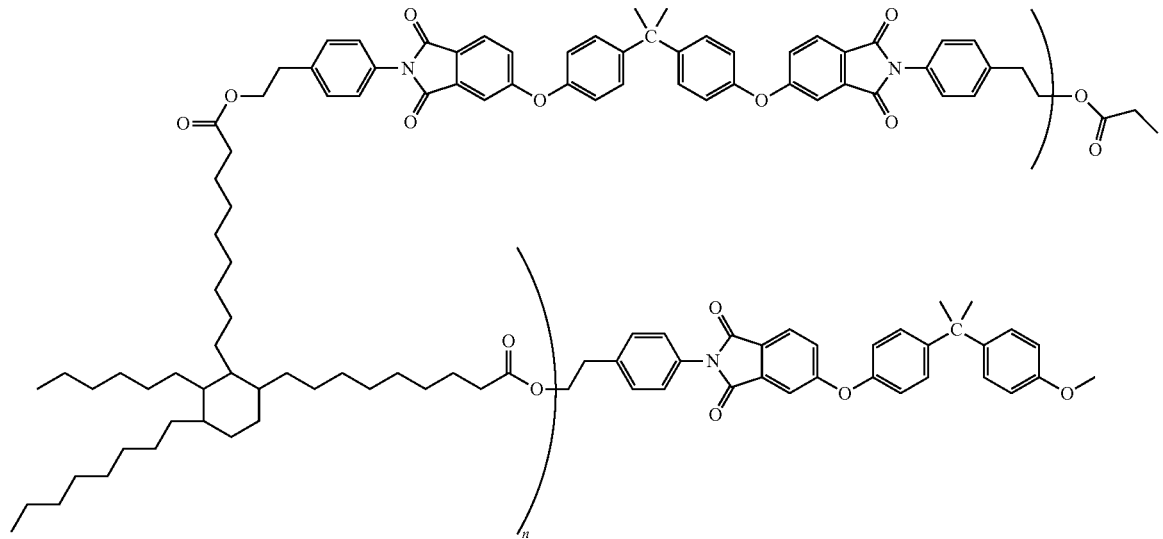

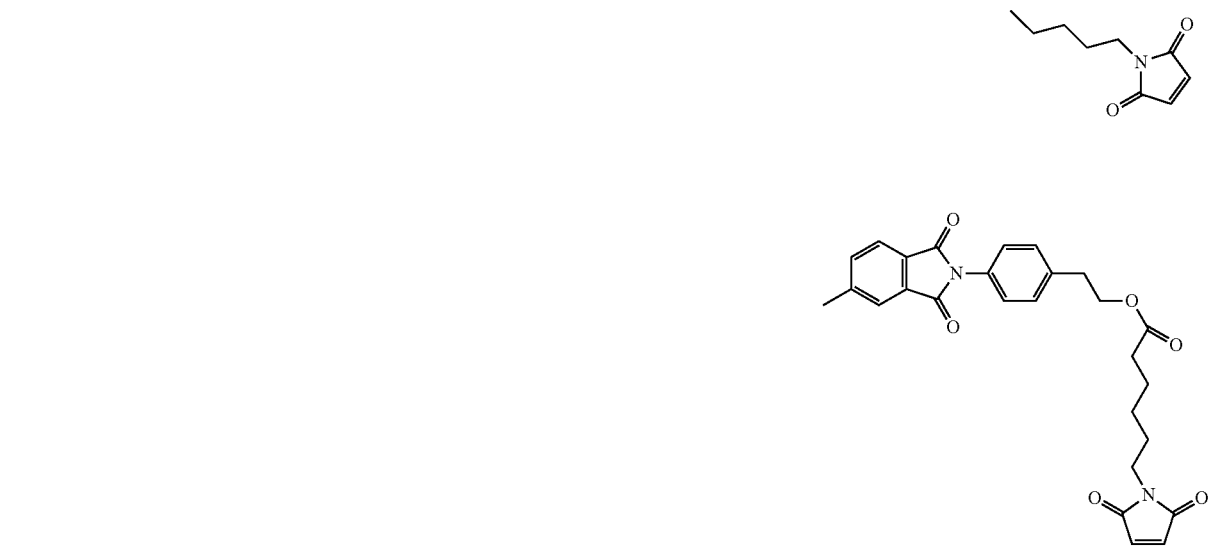

Dimer acid (EMPOL 1088 from St. Lawrence Chemicals) (15.4 grams, 0.0274 mol), intermediate from Example 2 (50.0 grams, 0.0658 mol), and toluene (150 mL) were charged to a 500 mL 4-neck round-bottom reaction flask equipped with a thermometer, mechanical mixer, condenser and Dean-Stark trap. The reaction flask was purged with nitrogen while mixing at 300 rpms in an oil bath preheated to 145° C. When the reaction temperature reached 80°-90° C., methanesulfonic acid (1.9 grams) was added. Shortly thereafter, the reaction started refluxing at 112° C. The nitrogen purge was removed and the reaction maintained at reflux temperature with mixing for two hours. Progress was monitored by water volume generated and collected in the Dean Stark trap. After two hours of refluxing, the reaction was allowed to cool to room temperature, the color at this point being nearly black. Upon cooling, MCA (17.3 grams, 0.0822 mol), methyl hydroquinone (0.017 grams), and toluene (50 mL) were added. The reaction was heated with mixing and refluxed for another four hours. As before, progress was monitored by water volume generated and collected in the Dean Stark trap. At the end of four hours the reaction was a dark brown mixture. The reaction did not filter well; therefore, the liquor was decanted from unwanted solids and 250 mL toluene was added. The result was a hazy gold brown dispersion. An exchange resin (22 grams) was added and the mixture was stirred mechanically for one hour. The reaction mixture was filtered resulting in a hazy dark copper solution. Silica gel (22 grams) was added to the reaction solution, the mixture was stirred mechanically for one hour and the silica gel was filtered out. The resulting hazy copper reaction solution was stripped of solvent on a roto-evaporator at 40° C. yielding a tan powder. Product structure was confirmed by $^1$HNMR, see FIG. 6. The melt-point of this material was 53° C. by DSC.

Example 7

Preparation of Oligomer from Intermediate from Example 2 and Methacrylic Acid

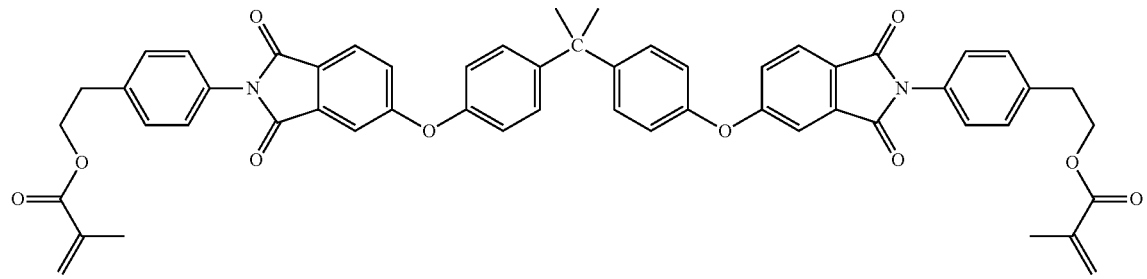

Methacrylic acid (10.00 grams, 0.1159 mol), intermediate from Example 2 (40.0 grams, 0.0527 mol), and toluene (150 mL) were charged to a 500 mL 4-neck round-bottom reaction flask equipped with a thermometer, mechanical mixer, condenser and Dean-Stark trap. The reaction flask was purged with nitrogen while mixing at 300 rpms in a hot oil bath preheated to 140° C. When the reaction temperature reached 80°-90° C., all solids were dissolved and sulfuric acid (0.49 grams) was carefully added. Shortly thereafter, the reaction started refluxing at 112° C. The nitrogen purge was removed and the reaction maintained at reflux with mixing for ten hours. Progress was monitored by measuring water volume generated and collected in the Dean Stark trap vs. theoretical (1.9 mL). During the reaction, some gel formed on the flask sides, the color of the reaction solution changed from dark olive green to cloudy gold, and 1.9 mL of water was collected in the Dean-Stark trap. Upon completion, the reaction was cooled and filtered yielding a grey cake and clear dark gold filtrate. An exchange resin (60 grams) was added to the filtrate and the mixture stirred mechanically for one hour. The reaction mixture was filtered, the filtration resulting in a yellow solution. The volume was adjusted to 600 mL with more toluene. Silica gel (60 grams) was added to the reaction solution and the mixture stirred mechanically for one hour. The silica gel was filtered out and 0.03 grams of methyl hydroquinone was added as a polymerization inhibitor. The resulting clear yellow reaction solution was stripped of solvent on a roto-evaporator at 40° C. yielding an amorphous yellow solid upon cooling. Product structure was confirmed by $^1$HNMR, see FIG. 7.

Example 8

Preparation of Oligomer from Intermediate from Example 1, MCA, and MPA

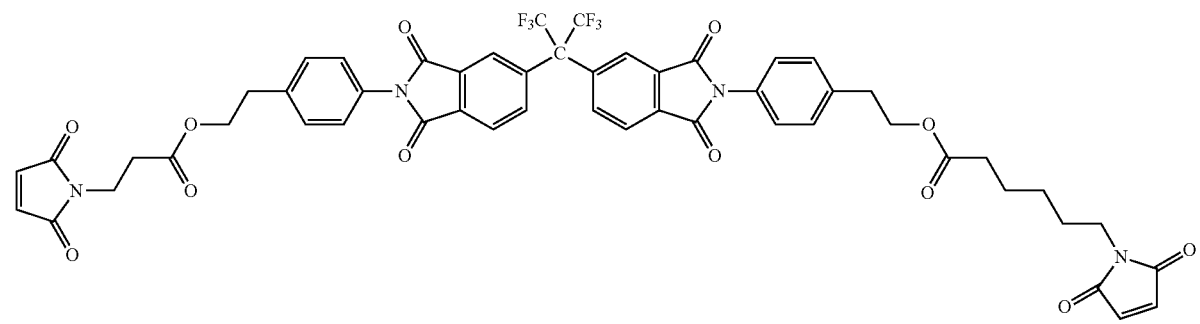

MCA (4.62 grams, 0.0219 mol), MPA (3.70 grams, 0.0219 mol), intermediate from Example 1 (13.0 grams, 0.0199 mol), and toluene (63 mL) were charged to a 250 mL 4-neck round-bottom reaction flask equipped with a thermometer, mechanical mixer, condenser and Dean-Stark trap filled with toluene. The reaction flask was purged with nitrogen while mixing at 300 rpms in a hot oil bath preheated to 140° C. When the reaction temperature reached 80°-90° C., all solids were dissolved and sulfuric acid (0.19 grams) was added. Shortly thereafter, the reaction started refluxing at 112° C. The nitrogen purge was removed and the reaction was maintained at reflux with mixing for ten hours. The reaction was monitored by measuring water volume generated and collected in the Dean Stark trap vs. theoretical (0.7 mL). During the reaction, some gel formed on the flask sides, the color of the reaction solution changed from clear gold to clear orange, and 0.7 mL of water was collected in the Dean-Stark trap. Upon completion, the reaction was filtered and an exchange resin (15 grams) was added to the filtrate. The mixture was stirred mechanically for one hour. The reaction mixture was filtered, the filtration resulting in an opaque yellow filtrate. Silica gel (15 grams) was added to the reaction solution and the mixture stirred mechanically for one hour. The silica gel was filtered out and the resulting clear yellow reaction solution stripped of solvent on a roto-evaporator at 60° C. The product was a foamy gold solid readily pulverized to a powder. The structure was confirmed by ¹HNMR, see FIG. 8. The melt-point of this material was 52° C. by DSC.

Example 9

Preparation of Adduct of bis-Phenol A Imide Diol, Adipic Acid and Maleimidocaproic Acid (MCA)

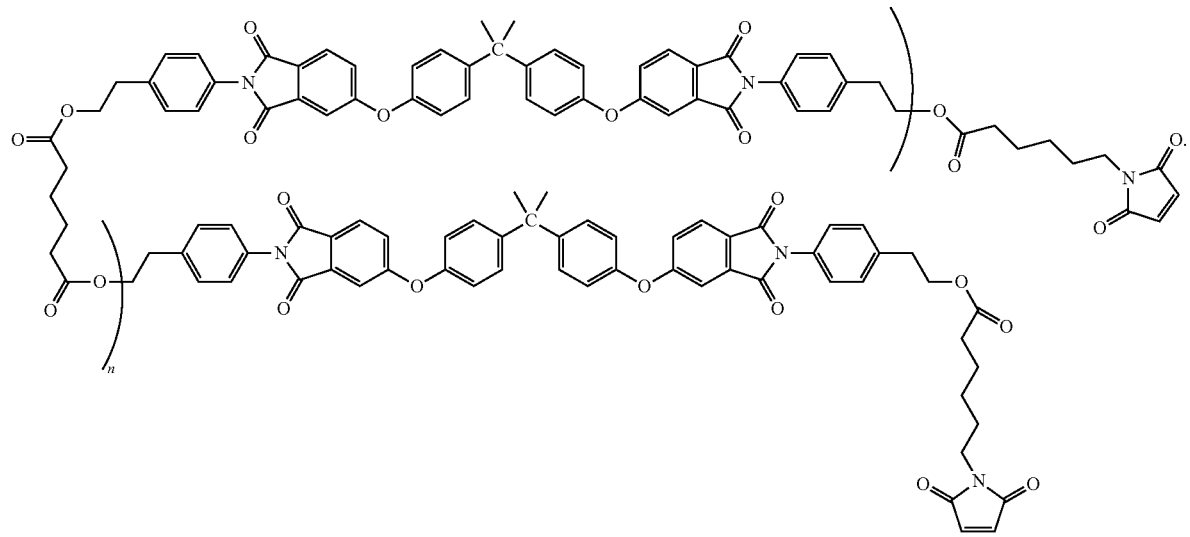

Adipic acid (4.82 grams, 0.0330 mol), bis-phenol A imide diol (60.0 grams, 0.0791 mol) and toluene (200 mL) were charged to a 1 L 4-neck round-bottom reaction flask equipped with a nitrogen purge, thermometer, mechanical mixer, condenser and Dean-Stark trap. The reaction flask is purged with nitrogen while mixing at 300 rpms in an oil bath preheated to 145° C. When the reaction temperature reached 80° C., methanesulfonic acid (2.32 grams) was carefully added. Shortly thereafter, the reaction started refluxing at ~106° C. The nitrogen purge was removed and the reaction maintained at reflux temperature with mixing for two hours. During the reaction, the color of the solution changed from opaque orange to a dark 2-phase dispersion and 1.2 mL of water was collected in the Dean-Stark trap.

The reaction was allowed to cool to room temperature. The top phase was grey and the bottom was black. MCA (20.9 grams, 0.0990 mol) was then added to the reaction while mixing at 300 rpms in an oil bath preheated to 145° C. The reaction was maintained at reflux temperature with mixing for 10 more hours. During this time, the theoretical total volume of water was collected in the Dean-Stark trap (2.6 mL). The reaction mix became a dark brown solution with some brown gel accumulated on the sides of the flask and foaming was observed. Brown and orange gel was filtered from the reaction at room temperature yielding a hazy gold-brown solution. The volume was increased from 200 mL to 400 mL with the addition of methylene chloride. This had the effect of clearing and homogenizing the hazy two-phase dispersion. The resin Amberlyst A-21 (44 grams) was added and the mixture stirred mechanically for one hour. Filtration of the resin A-21 was very slow. Next, 44 grams of silica gel were added and the mixture stirred mechanically for one hour. The silica gel was filtered out resulting in a hazy gold solution.

The solution was stripped of solvent on a roto-evaporator giving a foamy tan solid product. The product adduct was pulverized and dried in a vacuum oven at 60° C. and the structure is confirmed by ¹HNMR. As is typical of most MCA derivatives, Michael adducts make up the bulk of the impurities in this material. The melting point of the adduct was 95° C.

What is claimed is:

1. An alcohol having at least one imide moiety, which is the reaction product of an anhydride with an amino-alcohol in which (a) the anhydride is selected from the group consisting of 1,2,4-benzenetricarboxylic anhydride, cis-5-norbornene-endo-2,3-dicarboxylic anhydride, 1,2-cyclohexanedicarboxylic anhydride, cis-1,2,3,6-tetrahyydrophthalic anhydride, 3,4-pyridinedicarboxylic anhydride, homophthalic anhydride, 2-methylenesuccinic anhydride, methyl-5-norbornene-2,3-dicarboxylic anhydride, 3,1-benzoxazine-2,4(1H)-dione, 4,4'-(hexafluoro-isopropylidine)bisphthalic anhydride (6FDA), 4,4'-bisphenol A dianhydride, benzene-1,2,4,5-tetracarboxylic dianhydride, 1,4,5,8-naphthalenetetracarboxylic dianhydride, diethylenetriamine-pentaacetic acid dianhydride, bicyclo[2.2.2]oct-7-ene-2,3,5,6-tetracarboxylic dianhydride, perylene-3,4,9,10-tetracarboxylic dianhydride 3,3'4,4'-biphenyltetracarboxylic dianhydride, benzophenone-3,3'4,4'-tetracarboxylic dihydride, and maleic anhydride functionalized polybutadiene: and (b) the amino-alcohol is selected from the group consisting of 4-aminophenyl-ethanol, 3-amino-1-propanol, 2-amino-1-phenylethanol, (R)-2-amino-2-phenyl-ethanol, 1-(3-aminophenyl)ethanol, and 2-amino-3-methylbenzyl alcohol.

2. The alcohol according to claim 1 having the structure:

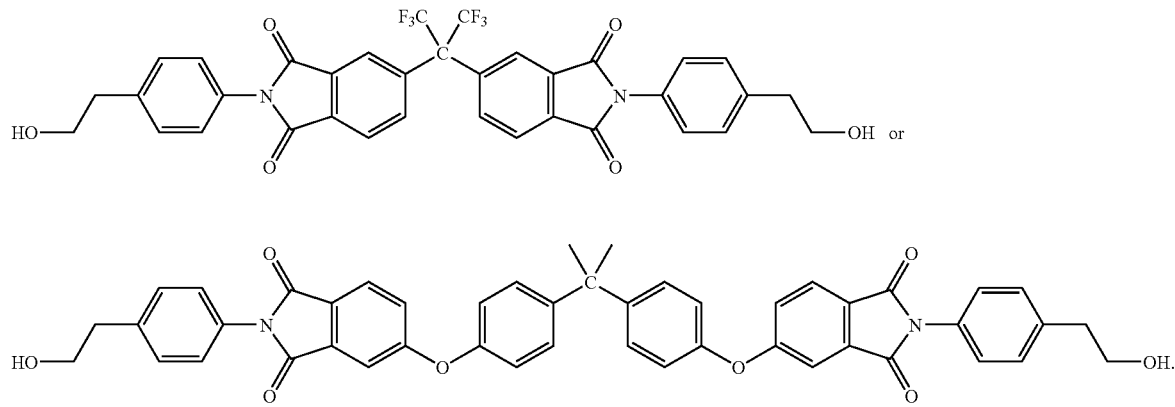

3. A reactive oligomer having at least one imide moiety and at least one ester moiety, which is the reaction product of 4,4'-bisphenol A dianhydride, 4-aminophenethyl alcohol, and a carboxylic acid having an additional reactive functionality selected from the group consisting of acrylate, methacrylate, styrene, cinnamyl, maleate, fumarate, propargyl ether, vinyl ether, epoxy, oxetane, benzoxazine, oxazoline, cyanate ester, and silane.

4. The reactive oligomer according to claim 3 having the structure:

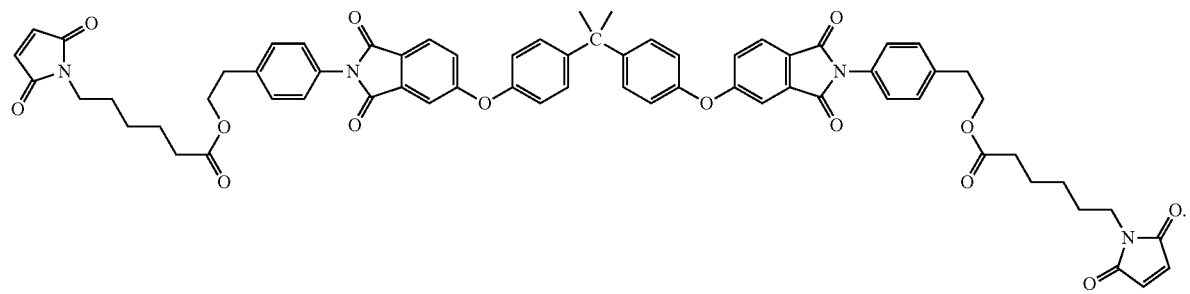

5. The reactive oligomer according to claim 3 having the structure:

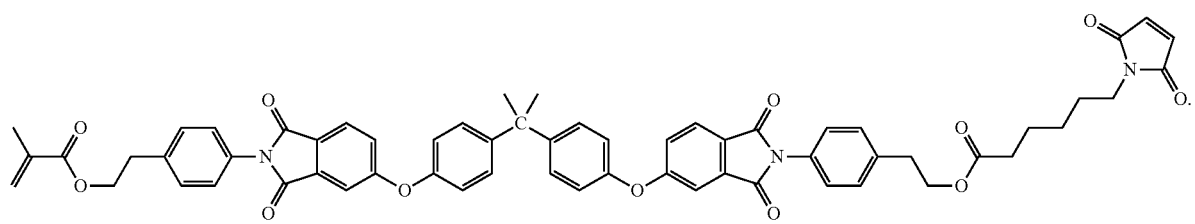

6. The reactive oligomer according to claim 3 having the structure:
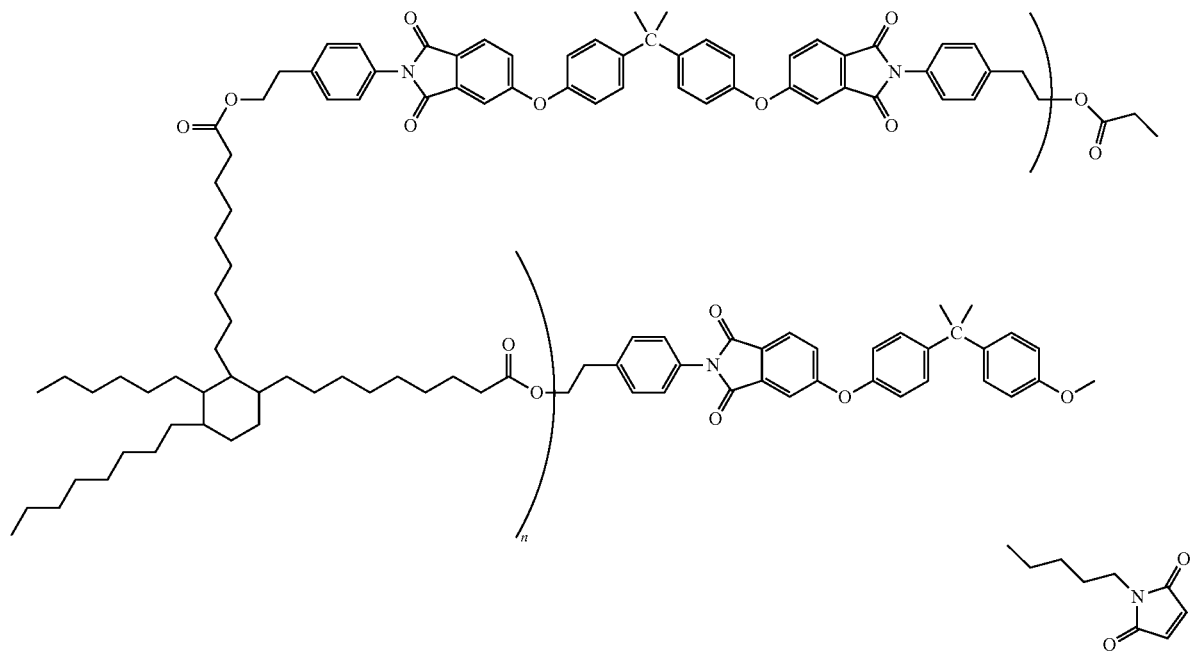
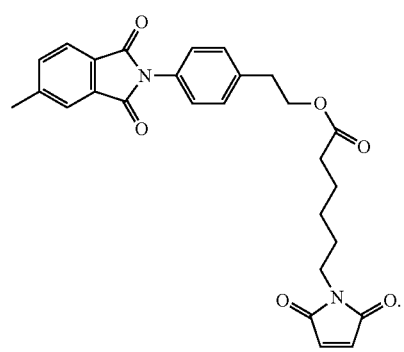
7. The reactive oligomer according to claim 3 having the structure:
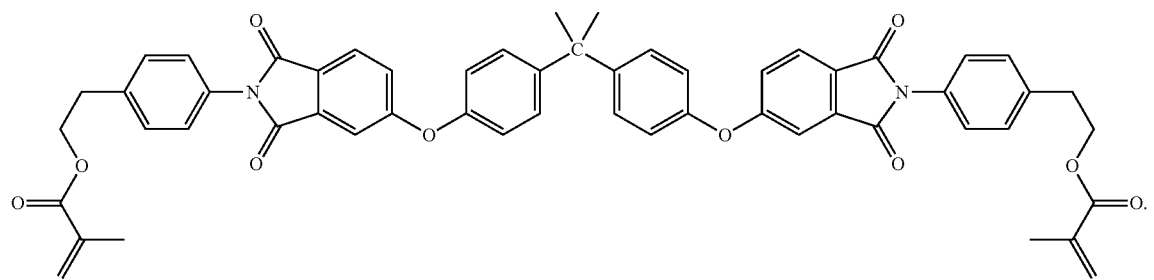

8. The reactive oligomer according to claim 3 having the structure
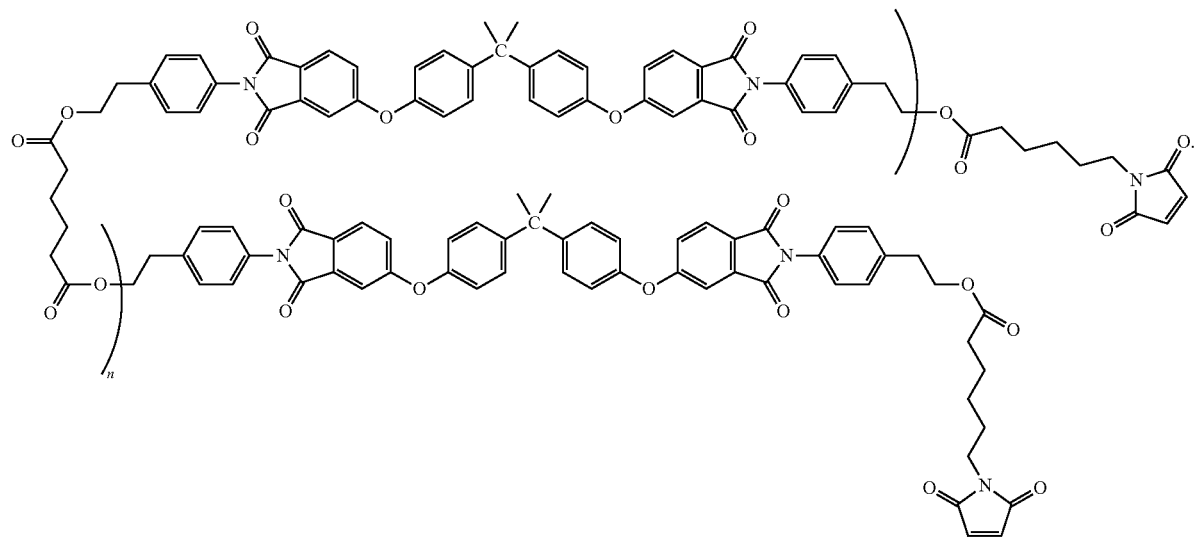
9. A curable composition comprising the reactive oligomer of claim 3.
* * * * *